(12) United States Patent
Freud et al.

(10) Patent No.: US 8,451,434 B2
(45) Date of Patent: May 28, 2013

(54) METHOD AND APPARATUS FOR MEASURING ZETA POTENTIAL OF SUSPENDED PARTICLES

(75) Inventors: Paul J Freud, Furlong, PA (US); Michael N Trainer, Coopersburg, PA (US)

(73) Assignee: Microtrac Inc., Montgomeryville, PA (US)

( * ) Notice: Subject to any disclaimer, the term of this patent is extended or adjusted under 35 U.S.C. 154(b) by 960 days.

(21) Appl. No.: 12/539,340

(22) Filed: Aug. 11, 2009

(65) Prior Publication Data

US 2011/0037980 A1    Feb. 17, 2011

(51) Int. Cl.
*G01P 3/36* (2006.01)

(52) U.S. Cl.
USPC ............................... 356/28; 356/28.5

(58) Field of Classification Search
CPC ............... G01C 3/00; G01C 3/08; G01P 3/36
USPC ............ 356/3.01–3.15, 4.01–4.1, 5.01–5.15, 356/6–22, 28, 28.5, 139.01–139.1
See application file for complete search history.

(56) References Cited

U.S. PATENT DOCUMENTS

| | | | | |
|---|---|---|---|---|
| 4,602,989 | A | 7/1986 | Culkin | 204/180.1 |
| 5,022,972 | A * | 6/1991 | David et al. | 204/549 |
| 5,094,526 | A | 3/1992 | Freud et al. | 356/28.5 |
| 5,094,532 | A | 3/1992 | Trainer et al. | 356/336 |
| 6,104,490 | A | 8/2000 | Trainer | 356/336 |
| 6,104,491 | A | 8/2000 | Trainer | 356/336 |
| 6,281,973 | B1 | 8/2001 | Trainer | 356/342 |
| 6,396,979 | B1 | 5/2002 | Freud et al. | 385/34 |
| 7,449,097 | B2 | 11/2008 | Sekiwa et al. | 204/603 |
| 2007/0206203 | A1 | 9/2007 | Trainer | 326/521 |
| 2008/0218738 | A1 | 9/2008 | Trainer | 356/72 |
| 2008/0221814 | A1 * | 9/2008 | Trainer | 702/70 |

FOREIGN PATENT DOCUMENTS

WO    WO 2005/099408    10/2005

* cited by examiner

*Primary Examiner* — Luke Ratcliffe
(74) *Attorney, Agent, or Firm* — Ohlandt, Greeley, Ruggiero & Perle, LLP

(57) ABSTRACT

A zeta potential measurement system comprising: a cell having a cell wall and bottom for holding suspended particles; an optical measurement probe having a probe tip comprising a transparent and conducting thin film coating which prevents ionic current from accumulating charge on the probe tip, and wherein the optical measurement probe is inserted through the cell wall such that the probe tip is in fluid communication with the sample; a counter electrode inserted through the cell wall opposite to the optical measurement probe; a laser source which is disposed so as to deliver light to the optical measurement probe via an optical directional coupler and optical waveguide; wherein the optical measurement probe focuses the light onto a front surface of the probe tip, such that the light reflected from the front surface of the optical measurement probe and light backscattered from particles in the sample are collected by the probe tip, and thereafter focused to a optical waveguide and delivered through the coupler to a photodetector; an electrical output of the photodetector is connected to a filtering and amplification module, wherein an analog output of the amplification module is connected to an analog-to-digital converter, wherein the analog-to-digital converter creates a digital data stream which is stored in a first memory; and a computer or microprocessor which calculates the frequency power spectrum from the stored digital data stream and stores the frequency power spectrum in a second memory, wherein the first and second memories can be either the same or different.

21 Claims, 7 Drawing Sheets

DOPPLER DISPLACEMENT

ELECTRIC FIELD=E →

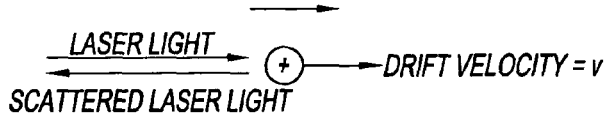

DRIFT VELOCITY = v

| DOPPLER DISPLACEMENT = SCATTERED LIGHT FREQUENCY SHIFT = (v/c) x $f_o$(LIGHT FREQUENCY) |
|---|

TYPICAL VALUES
$f_o$ = 10^14 Hz FREQUENCY OF INCIDENT LIGHT
MOBILITY = 4um/sec/V/cm, FIELD = 50 V/cm
v = .02 cm/sec DRIFT VELOCITY OF PARTICLE
Delta f = 100Hz DOPPLER DISPLACEMENT ZETA POTENTIAL CALCULATED FROM Delta f

POWER SPECTRUM AMPLITUDE METHOD

AC ELECTRIC FIELD = Eo SIN($f_{drive}$ x t)

PARTICLE MOTION
RANDOM BROWNIAN + BROWNIAN AT DRIVE FREQUENCY

POWER SPECTRUM AMPLITUDE METHOD = MEASUREMENT OF FULL POWER SPECTRUM 1Hz TO 40KHz DETERMINE THE AMPLITUDE RATIO OF RANDOM BROWNIAN TO RANDOM BROWNIAN AT DRIVE FREQUENCY

TYPICAL VALUES
DRIVE FREQUENCY = 2500Hz, DRIVE FIELD = 50V/cm
PARTICLE SIZE = 200 nanometers
MOBILITY = 4um/sec/V/cm
AMPLITUDE RATIO = .005

ZETA POTENTIAL CALCULATED FROM AMPLITUDE RATIO

*Fig. 8*

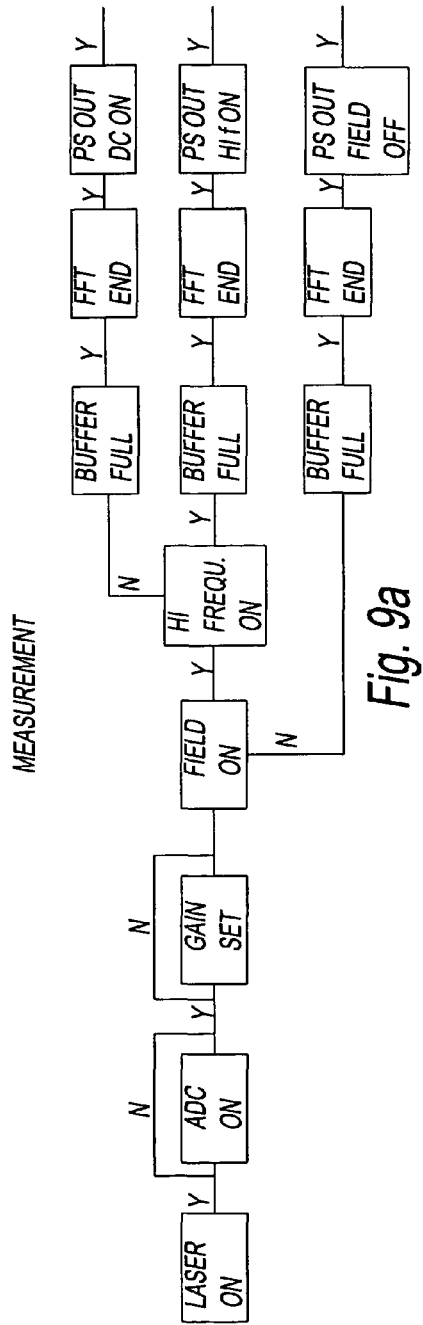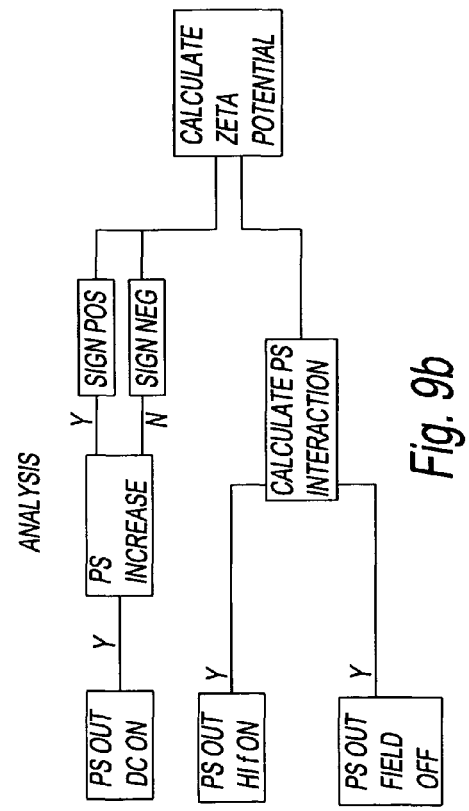

METHOD AND APPARATUS FOR MEASURING ZETA POTENTIAL OF SUSPENDED PARTICLES

BACKGROUND

1. Field of the Disclosure

The present disclosure relates generally to a method and apparatus for measuring a zeta potential of suspended particles. In particular, the apparatus is a zeta probe coated with a conducting and transparent thin film, wherein the film provides a path for ionic current to flow allowing an electric field to be applied between the probe and a counter electrode without surface charging. This probe configuration allows for the use of a high frequency AC electric field thereto which allows for the measuring of the magnitude of the interaction between the particle Brownian motion and the particle AC field motion and allows for the use of a DC field thereto which allows for the measuring of the sign of the zeta potential.

2. Discussion of the Background Art

Zeta potential is a measure of the charge on suspended particles and is a critical parameter in determining the stability of particle suspensions. Suspended particles with the same sign charge repel each other preventing particles from joining in agglomeration. The magnitude of the charge determines the degree of stability of the suspension. A means of determining the particle charge utilizes the response of particles to an applied electric field. Under the influence of an electric field charged particles move in response to the electric field force on the charged particle. In equilibrium with the viscous force of the suspending fluid the charged particles drift in the direction of the force at a drift velocity which is dependent on the charge, electric field and the viscosity of the suspending medium. A measurement of the drift velocity provides a means of determining the particle charge and the Zeta Potential.

U.S. Pat. Nos. 5,094,526 and 6,396,979 (which are incorporated by reference herein in their entirety) disclose an optical means of determining particle velocity. An optical probe inserted into a particle suspension delivers an optical beam into the suspension. The optical beam is backscattered by the suspended particles and the backscattered light is collected by the probe and transmitted by fiber optics to a photo detector. Also transmitted to the detector is a component of the optical beam which is Fresnel reflected from the probe suspending medium interface. The light scattered from the particles is Doppler frequency shifted due to the fact that the particles are in Brownian motion. The mixing of the frequency shifted scattered light with the reflected unshifted light at the photo detector results in a component of the photo detector output which is the difference frequency between the scattered light and the reflected light. The distribution of frequency shifts are measured as a frequency power spectrum and represent the distribution of velocities of the particles in Brownian motion. It is the purpose of the aforementioned patents to collect the distribution of the frequency shifts representing the distribution of velocities of the particles. From the distribution of velocities the size distribution of the suspended particles is calculated using the theories of dynamic light scattering. Disclosed in the aforementioned patents are the means of fabricating the optical probe which combines the scattered and reflected light, the use of a miniature optical element to transmit into the suspension and focus that light at the outer surface of a probe interface window, and the use of a window material to enhance the reflection at the interface.

Prior art shows how to optically measure particle motion and to measure that motion induced by the application of an electric field to suspended particles. Generally the particles are observed through a transparent wall in a sample containing cell. The motion is determined by measuring the Doppler Displacement of the optical beams light frequency. From the particles velocity, electric field and the fluid viscosity the particle electrophoretic mobility and charge can be calculated. Such a measurement is limited to optical paths within the measuring volume of the suspension which are not going to excessively attenuate the optical beam or multiscatter the scattered light. The prior art restricts the suspension to be very dilute or provides a complex external beam focusing to position the viewing volume close to a surface of the sample containing cell wall. Further the viewing volume must be positioned within the sample containing cell at a point which has negligible or non-interfering electroosmotic fluid flow.

An example of a prior art electrophoretic mobility measuring apparatus is disclosed in U.S. Pat. No. 7,449,097 (Sekiwa et al.) which is capable of conducting measurement with high sensitivity with optical attenuation reduced by incidence of light through the electrode face. This apparatus comprises a transparent electrode forming a part of a cell wall of a cell capable of confining a sample, and the other electrode opposite to the transparent electrode. A voltage is applied across these electrodes, and light is incident upon the inside of the cell through the transparent electrode. The scattering light which scatters from a sample S at a predetermined angle with respect to the incident angle, is received through the transparent electrode. The Doppler displacement is then measured based on the difference in frequency between the incident light and the outgoing light.

The problem associated with these prior art methods is that they measure particle velocity directly. In addition, direct current (DC) systems need to go into the solution to obtain an accurate measurement, need high electric fields to obtain an accurate reading, and ions in the solution tend to interfere with the DC reading. Alternating circuits (AC) operate at low frequency, but still exhibits some electro-chemical problems.

The present disclosure overcomes all of the electro-chemical interaction and problems exhibited by conventional electrophoretic mobility measuring apparatuses by the utilization of high frequency alternating current and by avoiding measurement of suspending fluid flow. In addition, the present disclosure provides a more accurate analysis than conventional zeta potential meters, requires no correction for electoosmonic flow, and can measure zeta potential at higher concentrations, whereas conventional cells must first dilute before measuring.

SUMMARY OF THE DISCLOSURE

In the present disclosure a probe is utilized to measure particle motion induced by electric field excitation of suspended particles. The probe inserted into a suspension is one electrode of a pair of electrodes. Electrical excitation between the two electrodes drives particles towards and away from the optical measurement probe which detects particle motion over a wide range of particle concentration. Because the probe fabrication technique precisely locates and fixes the optimum location of the viewing volume of the particle suspension at the outer surface of the probe's transparent window complex refocusing is not required to observe high concentration particle suspensions.

A method of measuring field induced particle motion at the probe surface, which method measures a combination of the particle Brownian motion and a high frequency electric field induced motion as a component of the total power spectrum at the electric field drive frequency.

A method of measuring the direction that particles move in an electric field and using such measured direction to determine the sign of the particles. The method measures the amplitude of the particle's Brownian motion power spectrum near to the probe surface viewing volume. Increasing or decreasing amplitude determines increasing or decreasing particle concentration, which in turn determines particle motion towards or away from the probe surface and hence determines particle charge sign. The same probe technology is used to insure that the particles are viewed at the surface where an electric field changes the particle concentration.

A zeta potential measurement system comprising: a cell having a cell wall and bottom for holding suspended particles; an optical measurement probe having a probe tip comprising a transparent and conducting thin film coating which prevents ionic current from accumulating charge on the probe tip, and wherein the optical measurement probe is inserted through the cell wall such that the probe tip is in fluid communication with the sample; a counter electrode inserted through the cell wall opposite to the optical measurement probe; a laser source which is disposed so as to deliver light to the optical measurement probe via an optical directional coupler and optical waveguide; wherein the optical measurement probe focuses the light onto a front surface of the probe tip, such that the light reflected from the front surface of the optical measurement probe and light backscattered from particles in the sample are collected by the probe tip, and thereafter focused to a optical waveguide and delivered through the coupler to a photodetector; an electrical output of the photodetector is connected to a filtering and amplification module, wherein an analog output of the amplification module is connected to an analog-to-digital converter, wherein the analog-to-digital converter creates a digital data stream which is stored in a first memory; and a computer or microprocessor which calculates the frequency power spectrum from the stored digital data stream and stores the frequency power spectrum in a second memory, wherein the first and second memories can be either the same or different.

Preferably, a voltage is applied between the optical measurement probe and the counter electrode to cause a high frequency AC field to be applied to the suspended particles to set the suspended particles in motion, thereby causing the velocity of the suspended particles and Brownian motion velocities to interact, thus causing a component of the Brownian motion frequency shift distribution to be measured around the frequency of the AC field.

When the suspended particles are excited by the high frequency AC field that an additional term is added to a power spectrum which is the result of the interaction between the Brownian motion velocities and the electric field induced motion, which is represented by the following general formula:

$$P(f)_{on} = A/(1+(f/f_o)^2) + \alpha A/(1+((f-f_{drive})/f_o)^2).$$

The frequency power spectrum is preferably calculated by the computer using a fourier transform analysis program.

The computer calculates a first power spectrum wherein an electrical excitation source is in the 'off' position and a second power spectrum wherein an electrical excitation source is in the 'on' position. When the excitation source is in the 'on' position, the computer controls the waveform of the excitation generated by the excitation source. The excitation from the excitation source is preferably a sine wave at about 2500 Hz and having an electric field of 50-100 volts/cm. When the excitation source is in the 'off' position, the frequency power spectrum is attributed to the Brownian motion of the suspended particles.

The shape of the frequency power spectrum caused by the Brownian motion of the suspended particles is Lorentzian and is represented by the general formula:

$$P(f)_{off} = A/(1+(f/f_o)^2)$$

wherein the frequency is f and the characteristic frequency, $f_o$, is a constant proportional to 1/(particle diameter).

A method for measuring a zeta potential of suspended particles, the method comprising:
 inserting an optical measurement probe, the optical measurement probe having a probe tip comprising a transparent and conducting thin film coating which prevents ionic current from accumulating charge on the probe tip, and a counter electrode into the suspended particles, such that the optical measurement probe and the counter electrode are disposed opposite one another;
 delivering a light to the optical measurement probe via an optical directional coupler and optical waveguide;
 focusing the light onto a front surface of the probe tip
 collecting light reflected from the front surface of the optical measurement probe and light backscattered from suspended particles, wherein the light is collected by the probe tip;
 delivering the collected light to a photodetector;
 filtering and amplifying an electrical output of the photodetector, thereby producing an analog output;
 converting the analog output to a digital data stream; and
 calculating a frequency power spectrum from the digital data stream.

The method further comprising: applying a voltage between the optical measurement probe and the counter electrode to cause a high frequency AC field to be applied to the suspended particles and to set the suspended particles in motion, thereby causing the velocity of the suspended particles and Brownian motion velocities to interact, thus causing a component of the Brownian motion frequency shift distribution to be measured around the frequency of the AC field.

The method further comprising: exciting the suspended particles by applying the high frequency AC field, such that an additional term is added to a power spectrum which is the result of the interaction between the Brownian motion velocities and the electric field induced motion, which is represented by the following general formula:

$$P(f)_{on} = A/(1+(f/f_o)^2) + \alpha A/(1+((f-f_{drive})/f_o)^2).$$

The method further comprising: calculating a first power spectrum wherein an electrical excitation source is in the 'off' position and a second power spectrum wherein an electrical excitation source is in the 'on' position. When the excitation source is in the 'on' position the excitation source controls the waveform of the excitation generated. The excitation from the excitation source is a sine wave at about 2500 Hz and having an electric field of no greater than 100 volts/cm. When the excitation source is in the 'off' position the frequency power spectrum is attributed to the Brownian motion of the suspended particles.

A system for determining the sign of charged suspended particles, the system comprising: a cell having a cell wall and bottom for holding suspended particles; an optical measurement probe having a probe tip comprising a transparent and conducting thin film coating which prevents ionic current from accumulating charge on the probe tip, and wherein the optical measurement probe is inserted through the cell wall such that the probe tip is in fluid communication with the sample; a counter electrode inserted through the cell wall opposite to the optical measurement probe; a laser source which is disposed so as to deliver light to the optical measurement probe via an optical directional coupler and optical waveguide; wherein the optical measurement probe focuses the light onto a front surface of the probe tip, such that the light reflected from the front surface of the optical measurement probe and light backscattered from particles in the sample are collected by the probe tip, and thereafter focused to a optical waveguide and delivered through the coupler to a photodetector; an electrical output of the photodetector is connected to a filtering and amplification module, wherein an analog output of the amplification module is connected to an analog-to-digital converter, wherein the analog-to-digital converter creates a digital data stream which is stored in a first memory; and a computer or microprocessor which monitors the concentration of the suspended particles by measuring the magnitude of the frequency shift distribution, the application of a DC electric field between the probe and a counter electrode and the measurement of an increase or decrease of the magnitude, thereby determining the sign of the charged particles.

The velocity per electric field is proportional to the charge of the suspended particles.

BRIEF DESCRIPTION OF THE DRAWINGS

FIG. 8 depicts the conventional Doppler displacement versus the power spectrum amplitude method according to the present disclosure;

FIG. 9a is a logic diagram that depicts the steps taken for the measurement of the power spectra; and FIG. 9b is a logic diagram that depicts the steps taken for the analysis of zeta potential and zeta potential sign.

DETAILED DESCRIPTION OF THE PREFERRED EMBODIMENT

Figure 1:
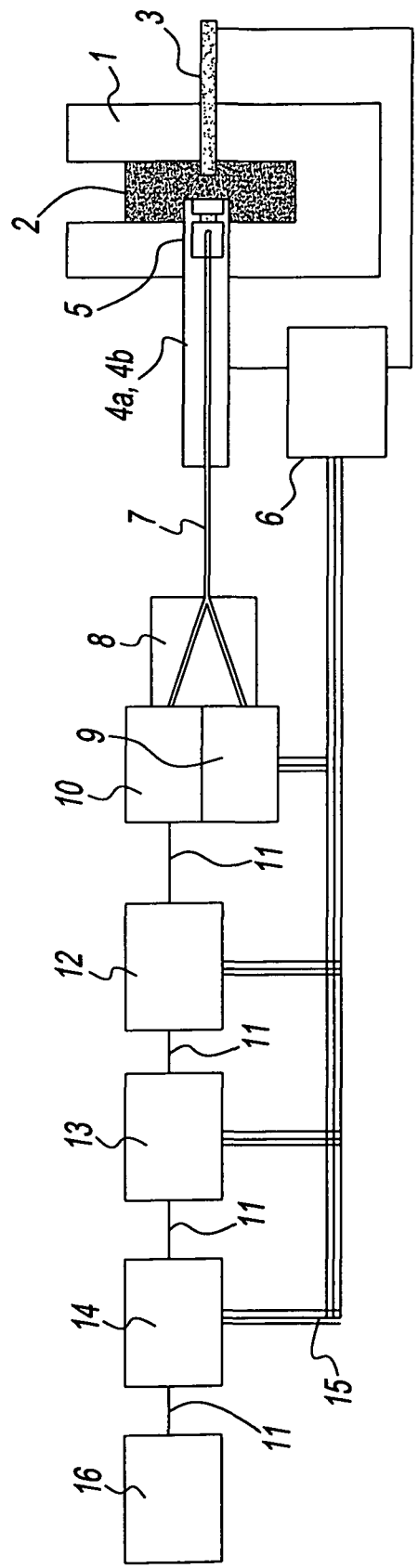
FIG. 1 is a block diagram of the Zeta Potential measurement system showing the relationship of the measurement cell and the optical measurement probe according to the present disclosure.

The present disclosure can best be described by reference to the figures, wherein FIG. 1 is a diagram of a preferred embodiment of the zeta potential measurement system. A sample cell 1 has an optical measurement probe 4a and 4b inserted through the cell wall and electrodes 3 inserted through the opposite cell wall. A particle suspension 2 is loaded into the sample cell covering the portion of the probe 4a and 4b and electrodes 3 inserted into the cell. Laser light from laser source 9 is delivered to the optical probe through optical directional coupler 8 and optical waveguide 7. The optical probe 4a or 4b focuses the laser light to the front surface of the optical probe tip 5. Light reflected from the front surface of probe tip 5 and light backscattered from the particle suspension 2 are collected by the probe tip focused to the optical waveguide 7 and delivered through the coupler 8 to the photodetector 10. The electrical output of the photodetector is connected to the filtering and amplification module 12. The analog output of module 12 is connected to the analog to digital converter 13 where the high speed analog-to-digital converter (ADC) creates a digital data stream stored in the memory (not shown) of computer 14. Computer or microprocessor 14 calculates the frequency power spectrum from the stored data using a fast Fourier transform analysis program. The power spectrum is stored in memory (not shown).

Figure 4:
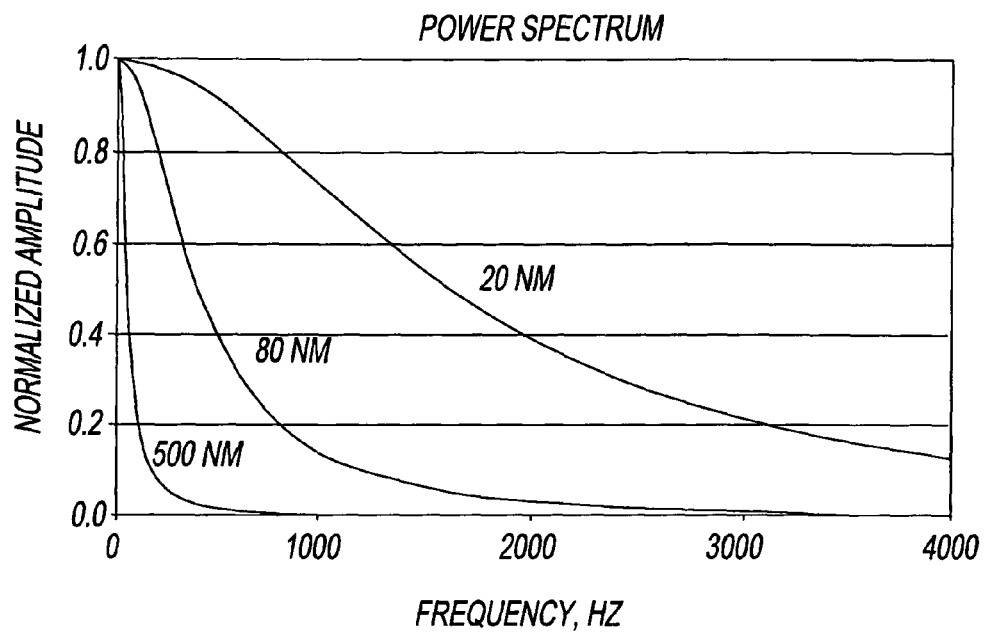
FIG. 4 is a graph of the frequency power spectrum for a 20 nm, 80 nm and 500 nm particles in a water suspension with the electric field excitation off.

Measurement of the zeta potential includes collecting two power spectrums, one with electrical excitation source 6 'off' and one with excitation source 6 'on'. In the 'on' state computer 14 controls the waveform of the excitation generated by excitation source 6. Preferred excitation for the zeta potential measurement is a sine wave at 2500 Hz and a max electric field of 100 volts/cm. The frequency power spectrum with the excitation off is attributed to the Brownian motion of the particles and is shown in FIG. 4 for three different particle sizes. From the theories of Brownian motion and dynamic light scattering it is known that the shape of the power spectrum is Lorentzian and of the form, $$P(f)_{off} = A/(1+(f/f_o)^2). \quad (1)$$

The frequency is f and the characteristic frequency, $f_o$, is a constant proportional to 1/(particle diameter). It was discovered and is the subject of this patent that when the suspension is excited by a high frequency sine wave electric field that an additional term is added to the power spectrum which is the result of the interaction between the particle Brownian motion and the particle electric field induced motion and is of the form, $$P(f)_{on} = A/(1+(f/f_o)^2) + \alpha A/(1+((f-f_{drive})/f_o)^2) \quad (2)$$

Figure 5:
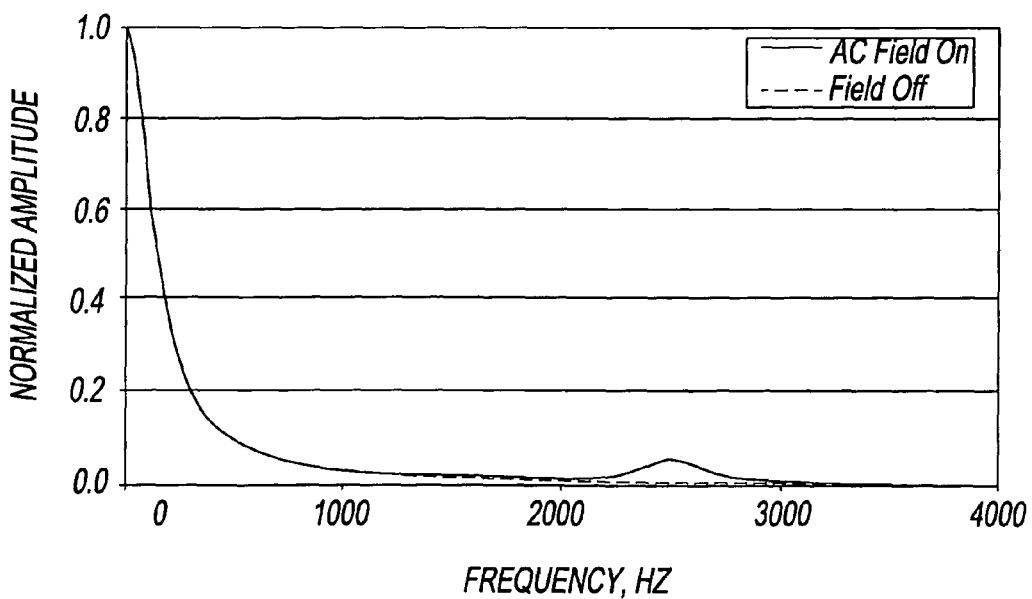
FIG. 5 is a graph of frequency power spectra for 500 nm particles with the electric field excitation off and on. The interaction term appears at the field drive frequency.
Figure 6:
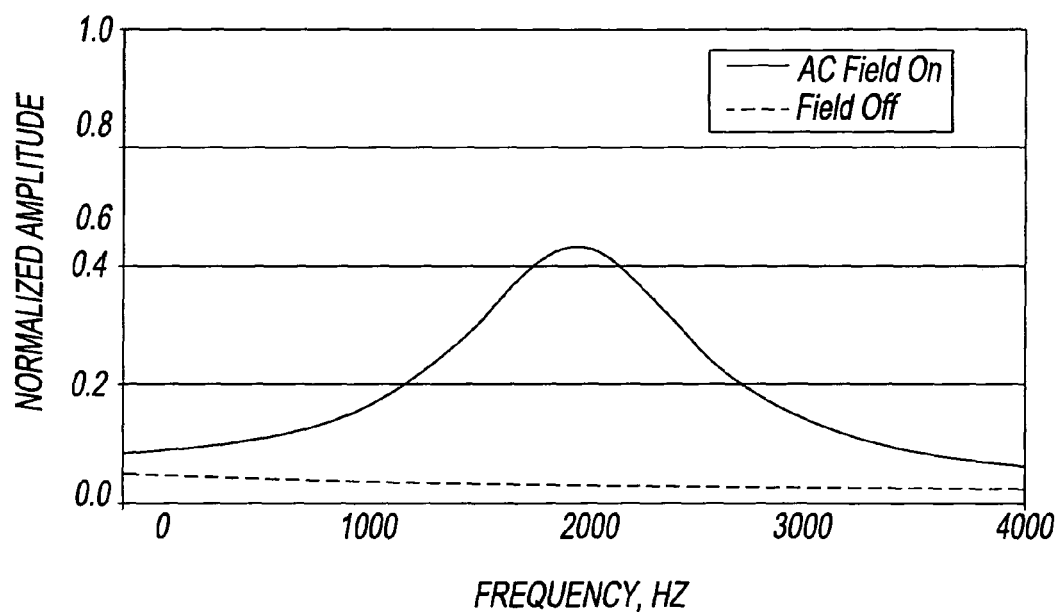
FIG. 6 is an expand scale graph of frequency power spectra for 500 nm particles with the electric field excitation off and on. The interaction term appears at the field drive frequency.

FIG. 5 shows an on power spectrum with excitation frequency, $f_{drive}$, at 2500 Hz. FIG. 6 shows the power spectrum on an expanded scale revealing the details of the interaction term. The interaction term appears at $f_{drive}$, the drive frequency of the excitation. The shape of the added term replicates the shape $P(f)_{off}$, the off power spectrum on either side of $f_{drive}$. The amplitude, $\alpha A$, of the interaction term is a fraction, $\alpha$, of the amplitude, $A$, of the off power spectrum. As part of this patent it was found that $\alpha$ is proportional to $(v_{particle})^2$. $v_{particle}$ is the particle velocity attributed to the electric field excitation. It is known from the theories of electrophoresis that the electrophoretic mobility, $\mu$, is related to the particle velocity and $\alpha$ by, $$\mu = (v_{particle})/\text{Electric field} = C(\alpha)^{1/2} \quad (3)$$

The zeta potential, ZP, is determined from the electrophoretic mobility.

$$ZP = (\eta/\in)\mu \quad (4)$$

The properties of the suspending medium, viscosity, $\eta$, and dielectric constant, $\in$, are required to determine zeta potential from mobility. See Equation 4. A zeta potential measurement is made using the zeta potential measurement system shown in FIG. 1 to measure and store a frequency power spectrum with excitation on and off. The amplitude of the power spectrum interaction term is determined from the excitation on and excitation off power spectra shown in FIGS. 4 and 5 and electrophoretic mobility and zeta potential are determined from the square root of the interaction term amplitude.

Figure 7A:
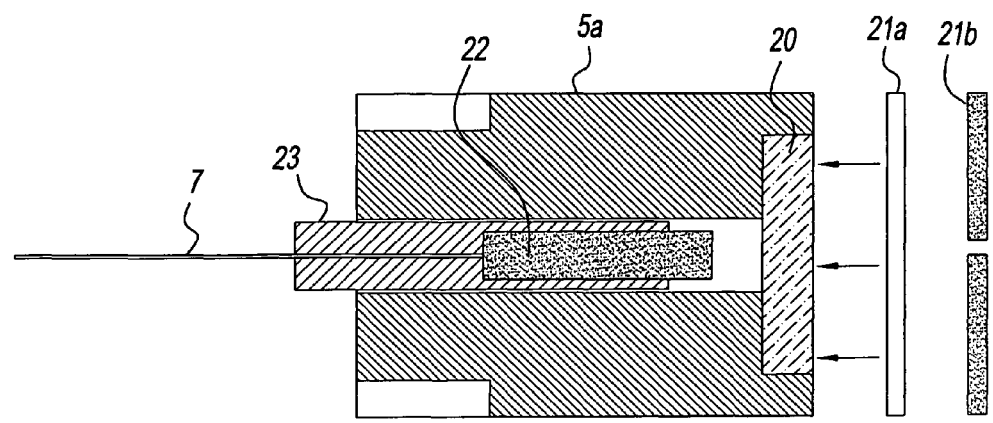
FIG. 7a is a diagram of the optical probe tip for use as a zeta potential magnitude probe showing the application of a transparent conducting layer and an opaque metal layer with optical opening according to one embodiment of the present disclosure.
Figure 7B:
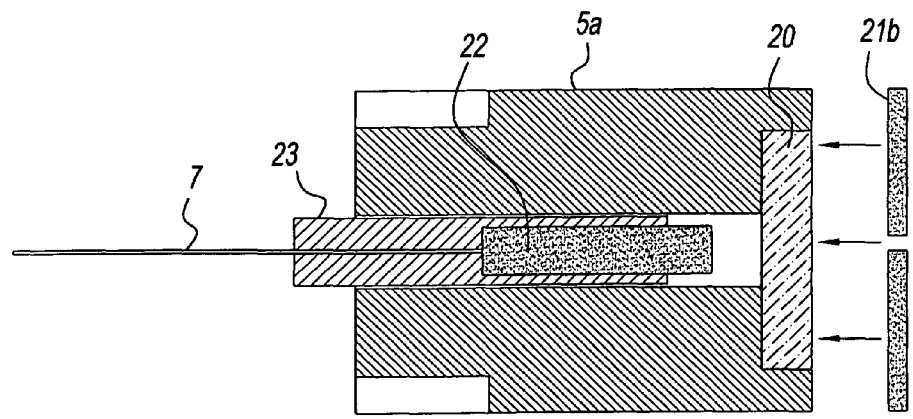
FIG. 7b is a diagram of the optical probe tip for use as a zeta potential sign probe showing the application of an opaque metal layer with optical opening according to another embodiment of the present disclosure.

The sign of the zeta potential is determined by the sign of the charge on the suspended particles. As part of the invention the sign is determined utilizing a second probe design 4b. FIG. 7b shows the fabrication of the probe tip 5b for probe 4b. An opaque gold film is deposited on the tip surface with a small opening at the point of focus of the input laser light. The transparent conducting film is not used for the sign determination probe to avoid degradation by DC current. The resulting configuration of metal film with opening avoids degradation if the sign of the voltage applied to the probe is negative and the metal is resistant to reduction as is gold. Field distortions due to the insulating surface of the opening do not effect the measurement of accumulation or depletion of particles. Fabrication of the probe includes focusing the laser light from the optical waveguide to the front surface of the probe tip 5b. This limits the region where particles are viewed to a volume close to the probe tip 5b surface. This configuration allows maximum particle concentration to be measured since the optical path length in the suspension is minimized. This feature of the probe design also allows the concentration of particles to be determined at or near the tip surface of probe. This provides the ability of probe 4b to measure high concentration samples without having to dilute, as well as allowing probe 4b to see accumulation or depletion since the surface is where particle flow beings or ends. From the theories of dynamic light scattering it is known that the amplitude, A, (Equation 1) of the frequency power spectrum is proportional to the average particle concentration in the region being measured. The application of an electric field to the suspended particles will cause the particles to move at a velocity given by Equation 3. If the probe is negative then positive particles have a velocity towards the tip surface of probe and positive particles will have a velocity away from the tip surface of probe. Over a period of time particles will accumulate or deplete at the surface depending upon the sign of their charge and the polarity of the probe. By monitoring the power spectrum amplitude, a measure of the particle concentration at the tip surface of probe 4b is made. To measure the sign of particle charge the preferred electrical excitation is a DC voltage. The excitation remains on for a period of time long enough for enough particles to move into or out of the measurement region at the tip surface of probe 5 to make a detectable change in the power spectrum amplitude. For typical samples and electric field strength this requires 1-50 seconds.

To measure the sign of the charge the zeta potential measurement system, FIG. 1, measures the frequency power spectrum with the electrical excitation off and stores the result. Excitation source 6 is turned on and connected to 4b. The preferred excitation for sign measurement is a DC voltage. The frequency power spectrum with excitation on is measured and stored. The amplitude of the on power spectrum is compared to the amplitude of the off power spectrum. If the amplitude ratio, $A_{on}/A_{off}$, is greater than 1, then particles are moving towards the probe and are negative. If $A_{on}/A_{off}$ is less than 1, then particles are moving away from probe and are negative.

If probe is negative and $A_{on}/A_{off}$ is less than 1, then the charge is negative     (5)

If probe is negative and $A_{on}/A_{off}$ is greater than 1, then the charge is positive     (6)

The preferred choice of waveform for particle excitation generated by excitation source 6 is determined by a number of factors. First factor is the measurement being performed, ZP magnitude or for ZP sign. For magnitude measurement the preferred waveform is high frequency sinusoidal. It is preferred that the frequency be higher than the half power point of the power spectrum shown in FIG. 4. This will minimize the interference of the Brownian motion power spectrum with the interaction term. From FIG. 4 the half power point for a 20 nanometer particle in water is approximately 1600 Hz. Larger particles would have lower half power points. A second reason for high frequency is to avoid interference from electro-osmotic fluid flow. It is known that at frequencies greater than 1000 Hz electro-osmotic flow does not have time to set up and is negligible. A third reason for high frequency is to reduce the effects of electrochemical activity at the electrodes and enhance the electrode lifetime. At frequencies greater than 1000-2000 Hz electrochemical changes are reversible from the positive to the negative portion to the sine wave excitation and little damage can occur to the electrode. Considering all these factors the preferred frequency for the magnitude measurement is greater than 2000 Hz.

In making a sign measurement the preferred waveform is pulsed DC. The pulse width is determined by the time it takes particles to move in or out of the viewing volume at the front surface of the measurement probe and make a detectable increase or decrease in particle concentration. For typical particle velocities this time is in the range of 1 to 100 seconds. Either polarity of voltage can be used. The preferred polarity depends upon the material on the front surface of the probe and how electrochemically stable is that material. If that material can be oxidized, then the polarity should be negative. If that material can be reduced, then the polarity should be positive.

Because of the different requirements for the probe used to measure amplitude of the Zeta Potential from the probe to measure the sign two separate probes are used, 4a for amplitude and 4b for sign.

Figure 2:
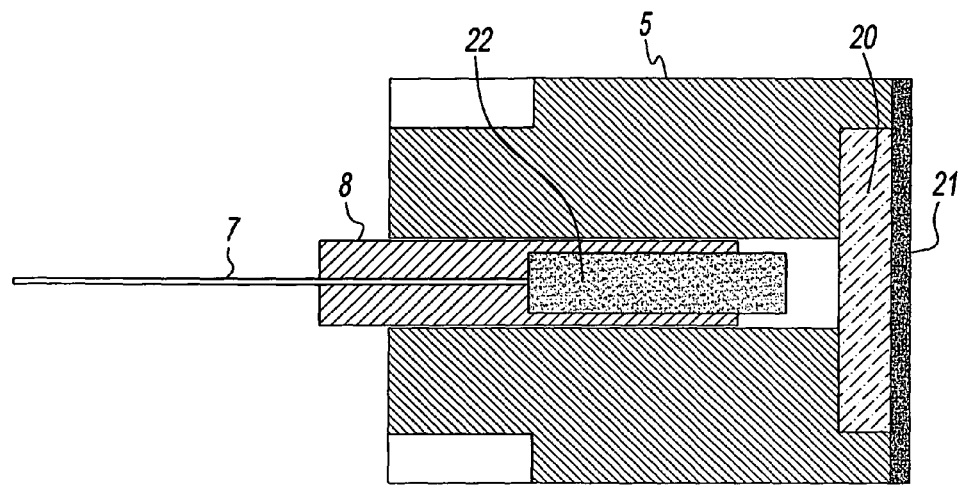
FIG. 2 is a diagram of the tip of the measurement probe showing the optical waveguide, focusing element, and transparent window according to the present disclosure.
Figure 3:
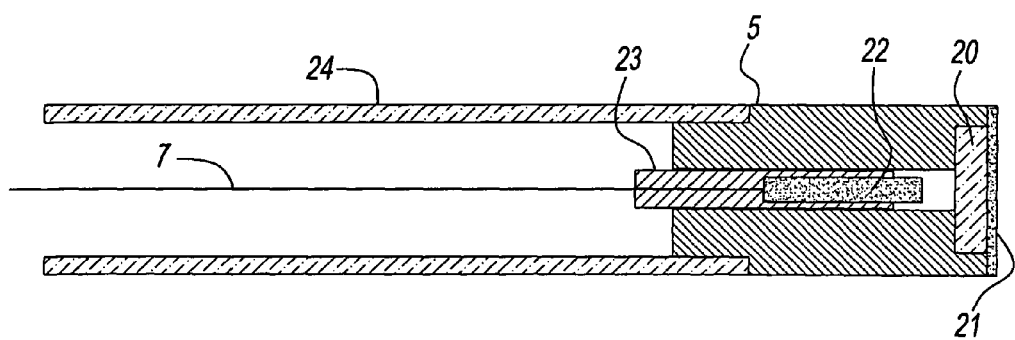
FIG. 3 is a diagram of the completed optical measurement probe according to the present disclosure.

The probe fabrication is described in U.S. Pat. Nos. 5,094,526 and 6,396,979, which are incorporated herein in their entirety. FIG. 3 shows the assembled probe design 4a or 4b. The optical waveguide 7 output is focused by lens element 22 to the outer surface of the transparent window 22 by moving sleeve element 8 towards and away from the window 22. At focus the miniature optical elements are fixed in place. Probe 4a or 4b are completed with a metal cover tube 24 attached thereto. FIG. 2 shows probe tip 5 assembled with the optical components fixed. Electrical excitation of probe 4a or 4b is made by connection of excitation source 6 to metal cover tube 24. In operation a typical suspension contains both charged particles and ions. Under excitation the ions move in parallel to the charged particles, positive ions towards the negative electrode and negative ions towards the positive electrode. If the electrode surface is insulating charges will accumulate on the surface and over time reduce the electric field acting on the suspension. In order to prevent charging, a conduction layer is applied to the outer surface of probe tip window 20. The conducting layer must be transparent in order to transmit the laser light into the suspension and collect the scattered light back scattered from the particles. An alternative to a conductive transparent layer is an opaque metal layer with an opening at the focal point of the laser light on the front surface of probe tip window 20. A third alternative is a combination of a conductive transparent layer under an opaque metal layer with an opening as shown in FIG. 7a. FIG. 7a shows the application of a transparent and conducting layer 21a and a metal layer 21b with an opening. This is the preferred configuration to be used to measure the amplitude when more current needs to be shunted away across the tip. FIG. 7b shows tip with an opaque metal layer with an opening 21b. This is the preferred configuration for measuring under DC conditions to obtain charge sign. A preferred material for a transparent and conducting layer would be at least one compound selected from the group consisting of: indium tin oxide, thin partially transparent inconel, nichrome, and chromium. A preferred material for a metal layer is at least one material selected from the group consisting of: gold, platinum, inconel, chromium, and nichrome.

FIG. 8 shows the conventional doppler displacement versus the power spectrum amplitude method of the present disclosure. The spectrum amplitude method measures at high frequency and avoids electrosmosis interference and electrochemical degradation. It is readily detected as a feature of the power spectrum located at the fixed field drive frequency and with the extent of the Brownian motion power spectrum. It varies only in amplitude relative to the unexcited Brownian motion power spectrum amplitude. Doppler displacement is limited to low frequency excitation due to the requirement to measure the displacement frequency over the period of the frequency to obtain an accurate measurement.

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. A zeta potential measurement system comprising:
a cell having a cell wall and bottom for holding suspended particles;
an optical measurement probe having a probe tip comprising a transparent and conducting thin film coating which prevents ionic current from accumulating charge on said probe tip, and wherein said optical measurement probe is inserted through said cell wall such that said probe tip is in fluid communication with a sample;
a counter electrode inserted through said cell wall opposite to said optical measurement probe;
a laser source which is disposed so as to deliver light to said optical measurement probe via an optical directional coupler and optical waveguide; wherein said optical measurement probe focuses said light onto a front surface of said probe tip, such that said light reflected from said front surface of said optical measurement probe and light backscattered from particles in said sample are collected by the probe tip, and thereafter focused to said optical waveguide and delivered through said optical directional coupler to a photodetector;
an electrical output of said photodetector is connected to a filtering and amplification module, wherein an analog output of said filtering and amplification module is connected to an analog-to-digital converter, wherein said analog-to-digital converter creates a digital data stream which is stored in a first memory; and
a computer or microprocessor which calculates the frequency power spectrum from said digital data stream which is stored in a first memory and stores said frequency power spectrum in a second memory, wherein said first memory and said second memory can be either the same or different.

2. The system according to claim 1, wherein a voltage is applied between said optical measurement probe and said counter electrode to cause a high frequency AC field to be applied to the suspended particles to set said suspended particles in motion, thereby causing the field induced velocity of the suspended particles and Brownian motion velocities to interact, thus causing a component of the Brownian motion frequency shift distribution to be measured around the frequency of the AC field.

3. The system according to claim 2, wherein when the suspended particles are excited by said high frequency AC field that an additional term is added to a power spectrum which is the result of the interaction between the Brownian motion velocities and the electric field induced motion, which is represented by the following general formula:

$$P(f)_{on} = A/(1+(f/f_o)^2) + \alpha A/(1+((f-f_{drive})/f_o)^2)$$

wherein $P(f)_{on}$ is the frequency (f) of a power spectrum wherein an electrical excitation source is in the 'on' position, the characteristic frequency ($f_o$) is a constant proportonal to 1/(particle diameter), $f_{drive}$ is the excitation frequency, A is the amplitude, and $\alpha A$ is a fraction, $\alpha$, of amplitude, A.

4. The system according to claim 1, wherein said frequency power spectrum is calculated by said computer or microprocessor using a Fourier transform analysis program.

5. The system according to claim 1, wherein said computer or microprocessor calculates a first power spectrum wherein an electrical excitation source is in the 'off' position and a second power spectrum wherein an electrical excitation source is in the 'on' position.

6. The system according to claim 5, when said electrical excitation source is in the 'on' position, said computer or microprocessor controls the waveform of the excitation generated by said excitation source.

7. The system according to claim 5, wherein the excitation from said electrical excitation source is a sine wave at about 2500 Hz and having an electric field of no greater than 100 volts/cm.

8. The system according to claim 5, when said electrical excitation source is in the 'off' position, said frequency power spectrum is attributed to the Brownian motion of the suspended particles.

9. The system according to claim 8, wherein the shape of said frequency power spectrum caused by the Brownian motion of the suspended particles is Lorentzian and is represented by the general formula:

$$P(f)_{off} = A/(1+(f/f_o)^2)$$

wherein $P(f)_{off}$ is the frequency (f) of a power spectrum wherein an electrical excitation source is in the 'off' position, A is the amplitude, the frequency is f and the characteristic frequency, $f_o$, is a constant proportional to 1/(particle diameter).

10. A method for measuring a zeta potential of suspended particles, said method comprising:
inserting an optical measurement probe, said optical measurement probe having a probe tip comprising a transparent and conducting thin film coating which prevents ionic current from accumulating charge on said probe tip, and a counter electrode into said suspended particles, such that said optical measurement probe and said counter electrode are disposed opposite one another;
delivering a light to said optical measurement probe via an optical directional coupler and optical waveguide;
focusing said light onto a front surface of said probe tip
collecting light reflected from said front surface of said optical measurement probe and light backscattered from suspended particles, wherein said light is collected by said probe tip;

delivering said light collected by said probe tip to a photodetector;
filtering and amplifying an electrical output of said photodetector, thereby producing an analog output;
converting said analog output to a digital data stream; and
calculating a frequency power spectrum from said digital data stream.

11. The method according to claim 10, further comprising:
applying a voltage between said optical measurement probe and said counter electrode to cause a high frequency AC field to be applied to the suspended particles and to set said suspended particles in motion, thereby causing the field induced velocity of the suspended particles and Brownian motion velocities to interact, thus causing a component of the Brownian motion frequency shift distribution to be measured around the frequency of the AC field.

12. The method according to claim 11, further comprising:
exciting said suspended particles by applying said high frequency AC field, such that an additional term is added to a power spectrum which is the result of the interaction between the Brownian motion velocities and the electric field induced motion, which is represented by the following general formula:

$$P(f)_{on} = A/(1+(f/f_o)^2) + \alpha A/(1+((f-f_{drive})/f_o)^2)$$

wherein $P(f)_{on}$ is the frequency (f) of a power spectrum wherein an electrical excitation source is in the 'on' position the characteristic frequency ($f_o$) is a constant proportional to 1/(particle diameter), $f_{drive}$ is the excitation frequency, A is the amplitude, and $\alpha A$ is a fraction, $\alpha$, of amplitude, A.

13. The method according to claim 10, wherein said frequency power spectrum is calculated by a computer using a fourier transform analysis program.

14. The method according to claim 10, further comprising:
calculating a first power spectrum wherein an electrical excitation source is in the 'off' position and a second power spectrum wherein an electrical excitation source is in the 'on' position.

15. The method according to claim 14, when said electrical excitation source is in the 'on' position, controlling the waveform of the excitation generated by said excitation source.

16. The method according to claim 14, wherein the excitation from said electrical excitation source is a sine wave at about 2500 Hz and having an electric field of no greater than 100 volts/cm.

17. The method according to claim 14, when said electrical excitation source is in the 'off' position, attributing said frequency power spectrum to the Brownian motion of the suspended particles.

18. The method according to claim 17, wherein the shape of said frequency power spectrum caused by the Brownian motion of the suspended particles is Lorentzian and is represented by the general formula:

$$P(f)_{off} = A/(1+(f/f_o)^2)$$

wherein $P(f)_{off}$ is the frequency (f) of a power spectrum wherein an electrical excitation source is in the 'off' position, A is the amplitude, the frequency is f and the characteristic frequency, $f_o$, is a constant proportional to 1/(particle diameter).

19. A system for determining the sign of charged suspended particles, said system comprising:
a cell having a cell wall and bottom for holding suspended particles;
an optical measurement probe having a probe tip comprising a conducting film with an optically transparent opening at the tip center which prevents ionic current from accumulating charge on said probe tip, and wherein said optical measurement probe is inserted through said cell wall such that said probe tip is in fluid communication with a sample;
a counter electrode inserted through said cell wall opposite to said optical measurement probe;
a laser source which is disposed so as to deliver light to said optical measurement probe via an optical directional coupler and optical waveguide;
wherein said optical measurement probe focuses said light onto a front surface of said probe tip, such that said light reflected from said front surface of said optical measurement probe and light backscattered from particles in said sample are collected by the probe tip, and thereafter focused to said optical waveguide and delivered through said optical directional coupler to a photodetector;
an electrical output of said photodetector is connected to a filtering and amplification module, wherein an analog output of said filtering and amplification module is connected to an analog-to-digital converter, wherein said analog-to-digital converter creates a digital data stream which is stored in a first memory; and
a computer or microprocessor which monitors the concentration of said suspended particles by measuring the magnitude of the frequency shift distribution, the application of a DC electric field between said probe and a counter electrode and the measurement of an increase or decrease of the magnitude, thereby determining the sign of the charged particles.

20. The system according to claim 19, wherein said conducting film is an electrically conducting and transparent film.

21. The system according to claim 19, wherein said conducting film is an electrically conducting and opaque film with an uncoated optically transparent opening at the tip center.

* * * * *